United States Patent
Zhou et al.

(10) Patent No.: US 11,760,988 B2
(45) Date of Patent: Sep. 19, 2023

(54) L-ASPARTATE ALPHA-DECARBOXYLASE MUTANT AND APPLICATION THEREOF

(71) Applicant: Jiangnan University, Wuxi (CN)

(72) Inventors: Zhemin Zhou, Wuxi (CN); Zhongmei Liu, Wuxi (CN); Li Zhou, Wuxi (CN); Wenjing Cui, Wuxi (CN); Wenqi Ye, Wuxi (CN); Junling Guo, Wuxi (CN); Chao Wang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 198 days.

(21) Appl. No.: 17/208,066

(22) Filed: Mar. 22, 2021

(65) Prior Publication Data

US 2021/0238576 A1 Aug. 5, 2021

Related U.S. Application Data

(63) Continuation of application No. PCT/CN2019/092292, filed on Jun. 21, 2019.

(30) Foreign Application Priority Data

Sep. 27, 2018 (CN) .......................... 201811131112.5
Oct. 23, 2018 (CN) .......................... 201811234783.4

(51) Int. Cl.
  *C12N 9/88* (2006.01)
  *C12P 13/06* (2006.01)
  *C12N 1/21* (2006.01)

(52) U.S. Cl.
  CPC .............. *C12N 9/88* (2013.01); *C12P 13/06* (2013.01); *C12Y 401/01011* (2013.01)

(58) Field of Classification Search
  None
  See application file for complete search history.

(56) References Cited

FOREIGN PATENT DOCUMENTS

| CN | 107828714 A | 3/2018 |
|----|-------------|--------|
| CN | 107988194 A | 5/2018 |
| CN | 109055346 A | 12/2018 |
| CN | 109402097 A | 3/2019 |

OTHER PUBLICATIONS

English-language machine translation of CN 109055346 A, 2018. (Year: 2018).*
English-language machine translation of CN107828714 A, 2018. (Year: 2018).*
Qin Mo et al. "Identification of mutations restricting autocatalytic activation of bacterial L-aspartate a-decarboxylase amino acids" Aug. 2, 2018, V50 ISSN 1438-2199, p. 1433-1440.
Yasuyuki Arakane et al. "Molecular and Functional Analyses of Amino Acid Decarboxylases Involved in Cuticle Tanning in Tribolium castaneum" The Journal of Biological Chemistry vol. 284, No. 24, pp. 16584-16594, Jun. 12, 2009.

* cited by examiner

*Primary Examiner* — Todd M Epstein
(74) *Attorney, Agent, or Firm* — IPRO, PLLC

(57) ABSTRACT

The disclosure discloses an L-aspartate α-decarboxylase mutant and application thereof, and belongs to the technical field of enzyme engineering. In the disclosure, lysine at position 221 of L-aspartate α-decarboxylase is mutated to arginine, glycine at position 369 is mutated to alanine, and the obtained new mutant enzymes have better temperature tolerance and are beneficial to industrial production. The K221R and G369A recombinant strains are subjected to high-density fermentation, and with sodium L-aspartate as a substrate, a whole cell catalytic reaction is carried out to prepare β-alanine. Compared with a chemical production method, the method has the advantages that the production process is safe and clean, and has no environmental pollution. Compared with a pure enzyme catalysis method, the method has the advantages that the operation is simple and convenient. The yield of the final product β-alanine reaches 91% and 90% respectively, and the concentration reaches 162.15 g/L and 160.42 g/L respectively.

7 Claims, 6 Drawing Sheets

Specification includes a Sequence Listing.

SEQUENCE LISTING

```
<160> NUMBER OF SEQ ID NOS: 8

<210> SEQ ID NO 1
<211> LENGTH: 540
<212> TYPE: PRT
<213> ORGANISM: Artificial sequence
<220> FEATURE:
<223> OTHER INFORMATION: Protein translated from synthetic DNA

<400> SEQUENCE: 1

Met Pro Ala Thr Gly Glu Asp Gln Asp Leu Val Gln Asp Leu Ile Glu
1               5                   10                  15

Glu Pro Ala Thr Phe Ser Asp Ala Val Leu Ser Ser Asp Glu Glu Leu
                20                  25                  30

Phe His Gln Lys Cys Pro Lys Pro Ala Pro Ile Tyr Ser Pro Val Ser
            35                  40                  45

Lys Pro Val Ser Phe Glu Ser Leu Pro Asn Arg Arg Leu His Glu Glu
        50                  55                  60

Phe Leu Arg Ser Ser Val Asp Val Leu Leu Gln Glu Ala Val Phe Glu
65                  70                  75                  80

Gly Thr Asn Arg Lys Asn Arg Val Leu Gln Trp Arg Glu Pro Glu Glu
                85                  90                  95

Leu Arg Arg Leu Met Asp Phe Gly Val Arg Ser Ala Pro Ser Thr His
                100                 105                 110

Glu Glu Leu Leu Glu Val Leu Lys Lys Val Val Thr Tyr Ser Val Lys
            115                 120                 125

Thr Gly His Pro Tyr Phe Val Asn Gln Leu Phe Ser Ala Val Asp Pro
        130                 135                 140

Tyr Gly Leu Val Ala Gln Trp Ala Thr Asp Ala Leu Asn Pro Ser Val
145                 150                 155                 160

Tyr Thr Tyr Glu Val Ser Pro Val Phe Val Leu Met Glu Glu Val Val
                165                 170                 175

Leu Arg Glu Met Arg Ala Ile Val Gly Phe Glu Gly Gly Lys Gly Asp
                180                 185                 190

Gly Ile Phe Cys Pro Gly Gly Ser Ile Ala Asn Gly Tyr Ala Ile Ser
            195                 200                 205

Cys Ala Arg Tyr Arg Phe Met Pro Asp Ile Lys Lys Arg Gly Leu His
        210                 215                 220

Ser Leu Pro Arg Leu Val Leu Phe Thr Ser Glu Asp Ala His Tyr Ser
225                 230                 235                 240

Ile Lys Lys Leu Ala Ser Phe Gln Gly Ile Gly Thr Asp Asn Val Tyr
                245                 250                 255
```

```
Leu Ile Arg Thr Asp Ala Arg Gly Arg Met Asp Val Ser His Leu Val
        260                 265                 270

Glu Glu Ile Glu Arg Ser Leu Arg Gly Ala Ala Pro Phe Met Val
        275                 280                 285

Ser Ala Thr Ala Gly Thr Thr Val Ile Gly Ala Phe Asp Pro Ile Glu
290                 295                 300

Lys Ile Ala Asp Val Cys Gln Lys Tyr Lys Leu Trp Leu His Val Asp
305                 310                 315                 320

Ala Ala Trp Gly Gly Gly Ala Leu Val Ser Ala Lys His Arg His Leu
                325                 330                 335

Leu Lys Gly Ile Glu Arg Ala Asp Ser Val Thr Trp Asn Pro His Lys
        340                 345                 350

Leu Leu Thr Ala Pro Gln Gln Cys Ser Thr Leu Leu Arg His Glu
        355                 360                 365

Gly Val Leu Ala Glu Ala His Ser Thr Asn Ala Ala Tyr Leu Phe Gln
    370                 375                 380

Lys Asp Lys Phe Tyr Asp Thr Lys Tyr Asp Thr Gly Asp Lys His Ile
385                 390                 395                 400

Gln Cys Gly Arg Arg Ala Asp Val Leu Lys Phe Trp Phe Met Trp Lys
                405                 410                 415

Ala Lys Gly Thr Ser Gly Leu Glu Lys His Val Asp Lys Val Phe Glu
                420                 425                 430

Asn Ala Arg Phe Phe Thr Asp Cys Ile Lys Asn Arg Glu Gly Phe Glu
                435                 440                 445

Met Val Ile Ala Glu Pro Glu Tyr Thr Asn Ile Cys Phe Trp Tyr Val
450                 455                 460

Pro Lys Ser Leu Arg Gly Arg Lys Asp Glu Ala Asp Tyr Lys Asp Lys
465                 470                 475                 480

Leu His Lys Val Ala Pro Arg Ile Lys Glu Arg Met Met Lys Glu Gly
                485                 490                 495

Ser Met Met Val Thr Tyr Gln Ala Gln Lys Gly His Pro Asn Phe Phe
                500                 505                 510

Arg Ile Val Phe Gln Asn Ser Gly Leu Asp Lys Ala Asp Met Val His
        515                 520                 525

Leu Val Glu Glu Ile Glu Arg Leu Gly Ser Asp Leu
        530                 535                 540

<210> SEQ ID NO 2
<211> LENGTH: 540
<212> TYPE: PRT
<213> ORGANISM: Artificial sequence
<220> FEATURE:
<223> OTHER INFORMATION: Protein translated from synthetic DNA

<400> SEQUENCE: 2

Met Pro Ala Thr Gly Glu Asp Gln Asp Leu Val Gln Asp Leu Ile Glu
1               5                   10                  15

Glu Pro Ala Thr Phe Ser Asp Ala Val Leu Ser Ser Asp Glu Glu Leu
            20                  25                  30

Phe His Gln Lys Cys Pro Lys Pro Ala Pro Ile Tyr Ser Pro Val Ser
        35                  40                  45

Lys Pro Val Ser Phe Glu Ser Leu Pro Asn Arg Arg Leu His Glu Glu
    50                  55                  60

Phe Leu Arg Ser Ser Val Asp Val Leu Leu Gln Glu Ala Val Phe Glu
65                  70                  75                  80
```

```
Gly Thr Asn Arg Lys Asn Arg Val Leu Gln Trp Arg Pro Glu Glu
                 85                  90                  95

Leu Arg Arg Leu Met Asp Phe Gly Val Arg Ser Ala Pro Ser Thr His
                100                 105                 110

Glu Glu Leu Leu Glu Val Leu Lys Lys Val Val Thr Tyr Ser Val Lys
                115                 120                 125

Thr Gly His Pro Tyr Phe Val Asn Gln Leu Phe Ser Ala Val Asp Pro
                130                 135                 140

Tyr Gly Leu Val Ala Gln Trp Ala Thr Asp Ala Leu Asn Pro Ser Val
145                 150                 155                 160

Tyr Thr Tyr Glu Val Ser Pro Val Phe Val Leu Met Glu Glu Val Val
                165                 170                 175

Leu Arg Glu Met Arg Ala Ile Val Gly Phe Glu Gly Gly Lys Gly Asp
                180                 185                 190

Gly Ile Phe Cys Pro Gly Gly Ser Ile Ala Asn Gly Tyr Ala Ile Ser
                195                 200                 205

Cys Ala Arg Tyr Arg Phe Met Pro Asp Ile Lys Lys Lys Gly Leu His
                210                 215                 220

Ser Leu Pro Arg Leu Val Leu Phe Thr Ser Glu Asp Ala His Tyr Ser
225                 230                 235                 240

Ile Lys Lys Leu Ala Ser Phe Gln Gly Ile Gly Thr Asp Asn Val Tyr
                245                 250                 255

Leu Ile Arg Thr Asp Ala Arg Gly Arg Met Asp Val Ser His Leu Val
                260                 265                 270

Glu Glu Ile Glu Arg Ser Leu Arg Glu Gly Ala Ala Pro Phe Met Val
                275                 280                 285

Ser Ala Thr Ala Gly Thr Thr Val Ile Gly Ala Phe Asp Pro Ile Glu
                290                 295                 300

Lys Ile Ala Asp Val Cys Gln Lys Tyr Lys Leu Trp Leu His Val Asp
305                 310                 315                 320

Ala Ala Trp Gly Gly Gly Ala Leu Val Ser Ala Lys His Arg His Leu
                325                 330                 335

Leu Lys Gly Ile Glu Arg Ala Asp Ser Val Thr Trp Asn Pro His Lys
                340                 345                 350

Leu Leu Thr Ala Pro Gln Gln Cys Ser Thr Leu Leu Leu Arg His Glu
                355                 360                 365

Ala Val Leu Ala Glu Ala His Ser Thr Asn Ala Ala Tyr Leu Phe Gln
                370                 375                 380

Lys Asp Lys Phe Tyr Asp Thr Lys Tyr Asp Thr Gly Asp Lys His Ile
385                 390                 395                 400

Gln Cys Gly Arg Arg Ala Asp Val Leu Lys Phe Trp Phe Met Trp Lys
                405                 410                 415

Ala Lys Gly Thr Ser Gly Leu Glu Lys His Val Asp Lys Val Phe Glu
                420                 425                 430

Asn Ala Arg Phe Phe Thr Asp Cys Ile Lys Asn Arg Glu Gly Phe Glu
                435                 440                 445

Met Val Ile Ala Glu Pro Glu Tyr Thr Asn Ile Cys Phe Trp Tyr Val
                450                 455                 460

Pro Lys Ser Leu Arg Gly Arg Lys Asp Glu Ala Asp Tyr Lys Asp Lys
465                 470                 475                 480

Leu His Lys Val Ala Pro Arg Ile Lys Glu Arg Met Met Lys Glu Gly
                485                 490                 495
```

Ser Met Met Val Thr Tyr Gln Ala Gln Lys Gly His Pro Asn Phe Phe
            500                 505                 510

Arg Ile Val Phe Gln Asn Ser Gly Leu Asp Lys Ala Asp Met Val His
        515                 520                 525

Leu Val Glu Glu Ile Glu Arg Leu Gly Ser Asp Leu
    530                 535                 540

<210> SEQ ID NO 3
<211> LENGTH: 1620
<212> TYPE: DNA
<213> ORGANISM: Artificial Sequence
<220> FEATURE:
<223> OTHER INFORMATION: Synthetic DNA

<400> SEQUENCE: 3

| | | | |
|---|---|---|---|
| atgccggcta ccggtgaaga ccaggacctg gttcaggacc tgatcgaaga accggctacc | 60 |
| ttctctgacg ctgttctgtc ttctgacgaa gaactgttcc accagaaatg cccgaaaccg | 120 |
| gctccgatct actctccggt ttctaagcca gttagcttcg aatctctgcc aaaccgtcgt | 180 |
| ctgcacgaag aattcctgcg ttcttctgtt gacgttctgc tgcaagaggc tgtcttcgaa | 240 |
| ggcaccaacc gtaaaaaccg tgttctgcag tggcgtgaac cggaagaact gcgtcgtctg | 300 |
| atggacttcg tgttcgttc tgctccgtct acccacgaag aactgctgga agttctgaaa | 360 |
| aaagttgtta cctactctgt aaaaccggt caccgtact tcgttaacca gctgttctct | 420 |
| gctgttgacc cgtacggtct ggttgctcag tgggctaccg acgctctgaa cccgtctgtt | 480 |
| tacacctacg aggtttctcc ggtcttcgtg ctgatggaag aagttgttct gcgtgaaatg | 540 |
| cgtgctatcg ttggtttcga aggtggtaaa ggtgacggta tcttctgccc gggtggttct | 600 |
| atcgctaacg ttacgctat ctcttgcgct cgttaccgtt tcatgccgga catcaaaaaa | 660 |
| agaggtctgc actctctgcc gcgtctggtt ctgttcacct ctgaagacgc tcactactct | 720 |
| atcaaaaaac tggcttcttt ccagggtatc ggtaccgaca cgtttacct gatccgtacc | 780 |
| gacgctcgtg gtcgtatgga cgtttctcac ctggttgaag aaatcgaacg ttctctgcgt | 840 |
| gaaggtgctg ctccgttcat ggtttctgct accgctggta ccactgttat aggtgcgttc | 900 |
| gacccgatcg agaaaatcgc tgacgtttgc agaaatatcc aactgtggct gcacgttgac | 960 |
| gctgcttggg tggtggtgc tctggttct gctaaacacc gtcacctgct gaaaggtatc | 1020 |
| gaacgtgctg actctgttac ctggaaccg cacaaactgc tgaccgctcc gcagcagtgc | 1080 |
| tctaccctgc tgctgcgtca cgaaggtgtt ctggctgaag ctcactctac aacgctgct | 1140 |
| tacctgttcc agaaagacaa attctacgac accaatacg acaccggtga caacacatc | 1200 |
| cagtgcggtc gtcgtgctga cgttctgaaa ttctggttca tgtggaaagc taaaggtacc | 1260 |
| tctggtctga aaaacacgt tgacaaagtt ttcgaaaacg ctcgtttctt caccgactgc | 1320 |
| atcaaaaacc gtgaaggttt cgaaatggtt atcgctgaac cggaatacac caacatctgc | 1380 |
| ttctggtacg ttccgaaatc tctgcgtggt cgtaaagacg aagctgacta caagacaaa | 1440 |
| ctgcacaaag ttgctccgcg tatcaaagaa cgtatgatga agaaggttc tatgatggtt | 1500 |
| acctaccagg ctcagaaagg tcacccgaac ttcttccgta tcgttttcca gaactctggt | 1560 |
| ctggacaaag ctgacatggt tcacctggtt gaagaaatcg aacgtctggg ttctgacctg | 1620 |

<210> SEQ ID NO 4
<211> LENGTH: 1620
<212> TYPE: DNA
<213> ORGANISM: Artificial Sequence
<220> FEATURE:

<223> OTHER INFORMATION: Synthetic DNA

<400> SEQUENCE: 4

| | | | | | |
|---|---|---|---|---|---|
| atgccggcta | ccgtgaaga | ccaggacctg | gttcaggacc | tgatcgaaga | accggctacc | 60 |
| ttctctgacg | ctgttctgtc | ttctgacgaa | gaactgttcc | accagaaatg | cccgaaaccg | 120 |
| gctccgatct | actctccggt | ttctaagcca | gttagcttcg | aatctctgcc | aaaccgtcgt | 180 |
| ctgcacgaag | aattcctgcg | ttcttctgtt | gacgttctgc | tgcaagaggc | tgtcttcgaa | 240 |
| ggcaccaacc | gtaaaaaccg | tgttctgcag | tggcgtgaac | cggaagaact | gcgtcgtctg | 300 |
| atggacttcg | tgttcgttc | tgctccgtct | acccacgaag | aactgctgga | agttctgaaa | 360 |
| aaagttgtta | cctactctgt | taaaaccggt | cacccgtact | tcgttaacca | gctgttctct | 420 |
| gctgttgacc | gtacggtct | ggttgctcag | tgggctaccg | acgctctgaa | cccgtctgtt | 480 |
| tacacctacg | aggtttctcc | ggtcttcgtg | ctgatggaag | aagttgttct | gcgtgaaatg | 540 |
| cgtgctatcg | ttggtttcga | aggtggtaaa | ggtgacggta | tcttctgccc | gggtggttct | 600 |
| atcgctaacg | gttacgctat | ctcttgcgct | cgttaccgtt | tcatgccgga | catcaaaaaa | 660 |
| aaaggtctgc | actctctgcc | gcgtctggtt | ctgttcacct | ctgaagacgc | tcactactct | 720 |
| atcaaaaaac | tggcttcttt | ccagggtatc | ggtaccgaca | cgtttacct | gatccgtacc | 780 |
| gacgctcgtg | gtcgtatgga | cgtttctcac | ctggttgaag | aaatcgaacg | ttctctgcgt | 840 |
| gaaggtgctg | ctccgttcat | ggtttctgct | accgctggta | ccactgttat | aggtgcgttc | 900 |
| gacccgatcg | agaaaatcgc | tgacgtttgc | cagaaataca | aactgtggct | gcacgttgac | 960 |
| gctgcttggg | gtggtggtgc | tctggtttct | gctaaacacc | gtcacctgct | gaaaggtatc | 1020 |
| gaacgtgctg | actctgttac | ctggaacccg | cacaaactgc | tgaccgctcc | gcagcagtgc | 1080 |
| tctaccctgc | tgctgcgtca | cgaagctgtt | ctggctgaag | ctcactctac | caacgctgct | 1140 |
| tacctgttcc | agaaagacaa | attctacgac | accaaatacg | acaccggtga | caaacacatc | 1200 |
| cagtgcggtc | gtcgtgctga | cgttctgaaa | ttctggttca | tgtggaaagc | taaaggtacc | 1260 |
| tctggtctgg | aaaaacacgt | tgacaaagtt | ttcgaaaacg | ctcgtttctt | caccgactgc | 1320 |
| atcaaaaacc | gtgaaggttt | cgaaatggtt | atcgctgaac | cggaatacac | caacatctgc | 1380 |
| ttctggtacg | ttccgaaatc | tctgcgtggt | cgtaaagacg | aagctgacta | caaagacaaa | 1440 |
| ctgcacaaag | ttgctccgcg | tatcaaagaa | cgtatgatga | agaaggttc | tatgatggtt | 1500 |
| acctaccagg | ctcagaaagg | tcacccgaac | ttcttccgta | tcgttttcca | gaactctggt | 1560 |
| ctggacaaag | ctgacatggt | tcacctggtt | gaagaaatcg | aacgtctggg | ttctgacctg | 1620 |

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA

<400> SEQUENCE: 5
ccggacatca aaaaagagg tctgcactct ctg         33

<210> SEQ ID NO 6
<211> LENGTH: 33
<212> TYPE: DNA
<213> ORGANISM: Artificial Sequence
<220> FEATURE:
<223> OTHER INFORMATION: Synthetic DNA

<400> SEQUENCE: 6

```
cagagagtgc agacctcttt ttttgatgtc cgg                                              33

<210> SEQ ID NO 7
<211> LENGTH: 32
<212> TYPE: DNA
<213> ORGANISM: Artificial sequence
<220> FEATURE:
<223> OTHER INFORMATION: Synthetic DNA

<400> SEQUENCE: 7
gctgcgtcac gaagctgttc tggctgaagc tc                                               32

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
gagcttcagc cagaacagct tcgtgacgca gc                                               32
```

US 11,760,988 B2

L-ASPARTATE ALPHA-DECARBOXYLASE MUTANT AND APPLICATION THEREOF

REFERENCE TO SEQUENCE LISTING

The instant application contains a Sequence Listing which was submitted in ASCII format via EFS-Web and is hereby incorporated by reference in its entirety. Said ASCII Copy, created on Mar. 18, 2021, is named "seq.txt" and is 14,927 bytes in size.

TECHNICAL FIELD

The disclosure relates to an L-aspartate α-decarboxylase mutant and application thereof, and belongs to the technical field of enzyme engineering.

BACKGROUND

β-alanine is the only β-type amino acid that exists in nature, and is widely used in medicine, food and chemical industry. In medicine, β-alanine is an important raw material for the synthesis of calcium pantothenate and also is one of the two amino acids used to synthesize carnosine. β-alanine can be used as a raw material to synthesize pamidronate sodium for inhibiting bone metastasis of malignant tumors and the drug balsalazide for inhibiting colitis. In food, β-alanine can be used to synthesize sweeteners, etc. In chemical industry, β-alanine can be used as an antidote for lead poisoning.

In industrial production, the main synthesis methods of β-alanine are an acrylic acid and acrylonitrile amination method or a β-aminopropionitrile hydrolysis method, but most of these methods require high temperature, high pressure, strong acid or strong alkali conditions. Moreover, the product purification steps are cumbersome, and the preparation process will pollute the environment. Biosynthesis methods mainly use L-aspartate α-decarboxylase, and with L-aspartic acid as a substrate, an α-carboxyl group is removed to generate β-alanine. Due to simple operation, few by-products and low pollution, biosynthesis methods have attracted wide attention in recent years.

The L-aspartate α-decarboxylase currently studied is mainly derived from prokaryotes, such as *E. coli, Mycobacterium tuberculosis*, and *Corynebacterium glutamicum*. However, the L-aspartate α-decarboxylase derived from prokaryotic generally has low enzyme activity. Studies have found that the L-aspartate α-decarboxylase derived from the eukaryotic Tribolium castaneum has high enzyme activity, but has poor stability. Therefore, improving the thermal stability of L-aspartate α-decarboxylase (TcADC) derived from *T. castaneum* is very important for the industrial synthesis of β-alanine.

SUMMARY

The first objective of the disclosure is to provide an L-aspartate α-decarboxylase mutant with an amino acid sequence as set forth in SEQ ID NO:1 or SEQ ID NO:2.

The second objective of the disclosure is to provide a gene encoding the L-aspartate α-decarboxylase mutant.

The third objective of the disclosure is to provide a cell expressing the L-aspartate α-decarboxylase mutant.

In one embodiment of the disclosure, an *E. coli* BL21 cell is included.

In one embodiment of the disclosure, PET 24a(+) is used as an expression vector.

In one embodiment of the disclosure, a construction method is: a gene encoding the L-aspartate α-decarboxylase mutant is ligated with an expression vector and transformed into *E. coli*.

In one embodiment of the disclosure, the gene encoding the L-aspartate α-decarboxylase mutant as set forth in SEQ ID NO:4 or SEQ ID NO:5 is ligated with an expression vector and transformed into *E. coli*.

The fourth objective of the disclosure is to provide a composition containing the L-aspartate α-decarboxylase mutant.

In one embodiment of the disclosure, the composition includes, but is not limited to, a protective agent.

The fifth objective of the disclosure is to provide application of the L-aspartate α-decarboxylase mutant or the cell in the production of β-alanine or β-alanine-containing products.

The sixth objective of the disclosure is to provide a method for producing β-alanine, the L-aspartate α-decarboxylase mutant, or the cell, or the composition is used as a catalyst, and sodium L-aspartate is used as a substrate to carry out a transformation reaction.

In one embodiment of the disclosure, with sodium L-aspartate as a substrate, the cell is used for fermentation, and a bacteria solution after the fermentation broth is used for whole cell transformation to produce β-alanine.

In one embodiment of the disclosure, the conditions for the fermentation of the recombinant *E. coli* are: the recombinant *E. coli* bacteria solution cultured for 6-8 h is inoculated into a culture medium in a fermenter at an inoculum concentration of 6-8%, and cultured at 35-38° C. When the $OD_{600}$ reaches 60-70, the temperature is reduced to 28-30° C., IPTG is added to a final concentration of 0.5-1 mmol/L, and the fermentation is ended after induction culture is carried out for 35-40 h.

In one embodiment of the disclosure, the whole cell transformation conditions are: in a 10 mL reaction system, recombinant *E. coli* cells with an $OD_{600}$ of 150-250 are added, the final concentration of PLP is 0.5-2 mmol/L, the temperature is adjusted to 35-37° C., and when the substrate reacts completely, a next batch of substrate is added.

The seventh objective of the disclosure is to provide a method for improving the stability of L-aspartate α-decarboxylase, specifically, lysine at position 221 of L-aspartate α-decarboxylase with the amino acid sequence as set forth in SEQ ID NO:3 is mutated to arginine, or glycine at position 369 is mutated to alanine.

The eighth objective of the disclosure is to provide application of the L-aspartate α-decarboxylase mutant, or the cell, or the composition in the fields of feed, food or pharmacy.

Beneficial Effects of the Disclosure

First, the L-aspartate α-decarboxylase mutants K221R (the amino acid sequence is as set forth in SEQ ID NO:1, and the nucleotide sequence encoding K221R is as set forth in SEQ ID NO:3) and G369A (the amino acid sequence is as set forth in SEQ ID NO:2, and the nucleotide sequence encoding G369A is as set forth in SEQ ID NO:4) provided by the disclosure have the residual enzyme activity of 44% and 40% respectively after treatment at 50° C. for 30 min. Compared with a control enzyme mutant with the residual enzyme activity of 20% after treatment at 50° C. for 30 min, the thermal stability of the mutants is significantly improved. Therefore, the L-aspartate α-decarboxylase mutants K221R and G369A provided by the disclosure have better enzymatic properties, and are beneficial to the production of β-alanine by biological methods.

Second, the disclosure obtains the L-aspartate α-decarboxylase strain K221R with high enzyme activity by constructing recombinant E. coli expressing the L-aspartate α-decarboxylase mutant, and the pure enzyme specific enzyme activity of the recombinant L-aspartate α-decarboxylase K221R is 349 U/mg. The recombinant strain is fermented at high density, with the sodium L-aspartate as the substrate, the whole cell catalytic reaction is carried out to prepare β-alanine, and the yield of the β-alanine reaches 162.15 g/L.

Figure 1:
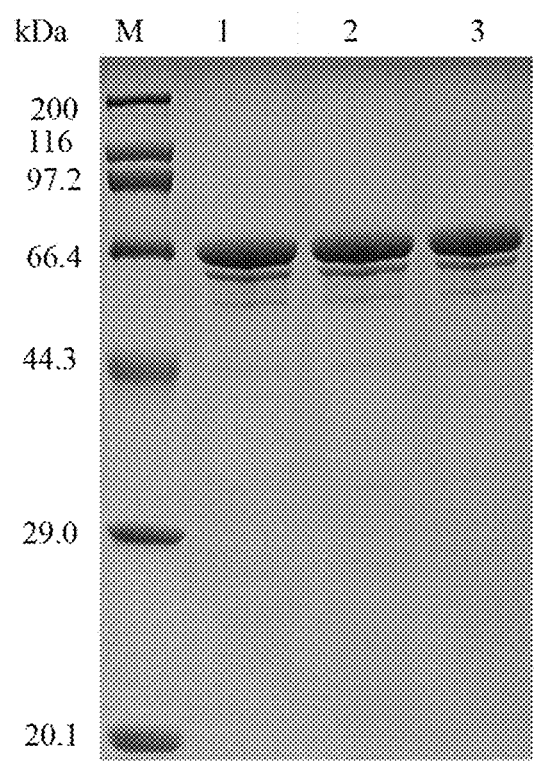
FIG. 1 is SDS-PAGE electrophoretogram of TcADC wild-type and mutant pure enzymes, in which M is the protein molecular weight standard; 1 is the wild-type purified protein; 2 is the K221R purified protein; and 3 is the G369A purified protein.

DETAILED DESCRIPTION (I) Determination Method of Enzyme Activity of L-Aspartate α-Decarboxylase Determination method of enzyme activity of fermentation broth: 100 μL of recombinant E. coli cells after fermentation are taken, 100 μl of 1 mol/L sodium L-aspartate solution is added, and 800 μL of phosphate buffer with a pH of 6.5 is added. After reacting at 37° C. for 30 min, reaction solution is inactivated at 100° C. for 10 min. The reaction solution is centrifuged at 12000 rpm for 2 min, the supernatant is taken for derivatization and the yield of β-alanine is detected. The reaction solution is filtered through a 0.22 μm microporous filter membrane and loaded onto a C18 chromatographic column for HPLC analysis.

Determination method of enzyme activity of L-aspartate α-decarboxylase: an appropriate amount of enzyme solution is added to a 1.5 mL centrifuge tube. Sodium L-aspartate at a final concentration of 100 mmol/L is added. The final concentration of PLP is 1 mmol/L, and the enzyme activity is detected after reacting at 37° C. and pH 6.5 for 30 min.

(II) Culture Medium

LB culture medium (g/L): peptone 10.0, yeast powder 5.0, NaCl 10.0.

2YT culture medium (g/L): peptone 16.0, yeast powder 10.0, NaCl 5.0.

Fermenter culture medium (g/L): glycerol 8.0, potassium dihydrogen phosphate 13.5, diammonium hydrogen phosphate 4.0, citric acid 1.7, magnesium sulfate heptahydrate 1.7, trace elements 10 mL.

Feed-batch culture medium (g/L): glycerol 500.0, magnesium sulfate heptahydrate 7.4, yeast powder 4.0, tryptone 4.0.

Trace elements (g/L): ferrous sulfate heptahydrate 10.0, zinc sulfate heptahydrate 2.3, copper sulfate pentahydrate 10.0, manganese sulfate tetrahydrate 0.5, borax 0.2, calcium chloride 2.0, ammonium molybdate 0.1.

(III) Method for Detecting the Content of Sodium L-Aspartate and β-Alanine by HPLC The reaction solution is derivatized with phenyl isothiocyanate (PITC). The specific steps are: 500 μL of the reaction solution is put into a 2.0 mL centrifuge tube. 250 μL of 0.1 mol/L PITC-acetonitrile solution and 250 μL of 1 mol/L triethylamine-acetonitrile solution are added and mixed thoroughly. The reaction solution is stored in the dark at room temperature for 1.0 h. 750 μL of n-hexane solution is added to terminate the derivatization. The reaction solution is shaken with a vortex shaker for 1 min, and allowed to stand for 30-60 min. The lower layer solution is pipetted and filtered through a 0.22 μm organic filter membrane, and then the sample is injected at a sample volume of 10 μL.

The derivatized product is determined by HPLC: the chromatographic column is La Chrom C18 (5 μm, 4.6×250 mm). A mobile phase A solution is 80% (V/V) acetonitrile aqueous solution, and a B solution is 97:3 (V/V, pH 6.5) 0.1 mol/L sodium acetate-acetonitrile solution. Gradient elution is adopted: during 0-20 min, the B solution is dropped from 95% to 65%; during 20-30 min, the B solution is raised from 65% to 95%; and during 30-35 min, the B solution gradient is not changed. The detection wavelength is 254 nm, and the column temperature is 40° C.

(IV) Determination of Temperature Stability

The wild-type enzyme is used as a control. The wild enzyme and the mutant enzyme are placed in phosphate buffers with a pH of 6.5, and incubated at 0° C., 20° C., 30° C., 40° C., 50° C., and 60° C. respectively for 30 min, and then the residual enzyme activity is determined to obtain the temperature stability results.

Example 1 Construction of Recombinant E. coli (1) Construction of mutants BL21/pET28a-K221R and BL21/pET28a-G369A: PCR was performed under the conditions shown in Table 1 with pET28a-TcADC plasmids as templates. The sequence information of the forward and reverse primers used to construct the mutant K221R is as set forth in SEQ ID NO:5 and SEQ ID NO:6 respectively. The sequence information of the forward and reverse primers used to construct the mutant G369A is as set forth in SEQ ID NO:7 and SEQ ID NO:8 respectively.

TABLE 1

| Whole plasmid PCR amplification reaction system | |
|---|---|
| Reagent | Amount (μL) |
| pET-28a-TcADC plasmids | 0.5 |
| Forward primer | 1.0 |

TABLE 1-continued

Whole plasmid PCR amplification reaction system

| Reagent | Amount (μL) |
| --- | --- |
| Reverse primer | 1.0 |
| ddH$_2$O | 22.5 |
| Total | 25 |

PCR Amplification Reaction Conditions:

95° C. Initial denaturation 5 min  
98° C. Denaturation 10 s  
56° C. Annealing 30 s  } 24 cycles  
72° C. Extension 75 s  
72° C. Extension 5 min The PCR products were identified by an agarose gel electrophoresis method. The PCR amplified products were transformed into E. coli JM109 competent cells to obtain recombinant plasmids pET28a-K221R and pET28a-G369A carrying the genes encoding the mutants. The recombinant plasmids pET28a-K221R and pET28a-G369A were respectively transformed into E. coli BL21 cells to obtain recombinant strains BL21/pET28a-K221R and BL21/pET28a-G369A.

(2) The recombinant E. coli BL21/pET28a-K221R and BL21/pET28a-G369A were respectively inoculated into 5 mL of LB culture medium containing kanamycin at a concentration of 50 μg/mL, and cultured overnight at 37° C. and 200 rpm with shaking.

(3) Expression and purification of L-aspartate α-decarboxylase

The recombinant E. coli BL21/pET28a-K221R and BL21/pET28a-G369A were respectively inoculated into 5 mL of LB culture medium containing kanamycin at a concentration of 50 μg/mL, and cultured overnight at 37° C. and 200 rpm with shaking. The overnight culture was inoculated into the 2YT culture medium containing kanamycin at a concentration of 50 μg/mL at an inoculum concentration of 1% (v/v), and cultured with shaking at 37° C. and 200 rpm until the OD$_{600}$ of the bacteria solution was 0.6-0.8. IPTG with a final concentration of 0.2 mmol/L was added and induction culture was carried out at 20° C. for about 20 h. Bacterial cells were collected by centrifugation at 6000 rpm, and ultrasonically broken. Protein purification was carried out using a His Trap HP affinity column. The target protein was detected by SDS-PAGE. The results are shown in FIG. 1.

(4) Determination of thermal stability

Figure 2:
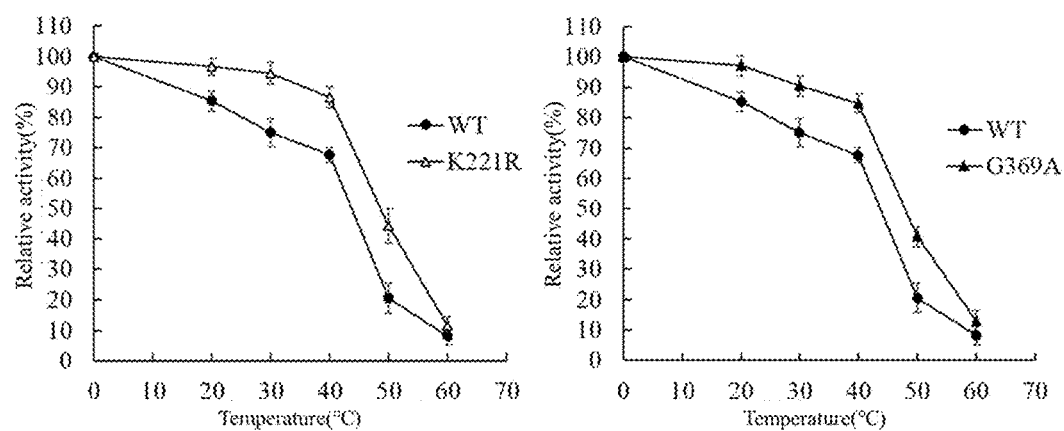
FIG. 2 shows thermal stability curves of enzymes after incubation at different temperatures.

The purified enzyme was diluted to the same concentration, treated at 0° C., 20° C., 30° C., 40° C., 50° C., and 60° C. for half an hour respectively, then reacted at 37° C. for half an hour, and then placed at 100° C. for ten minutes to terminate the reaction. The results are shown in FIG. 2.

Figure 3:
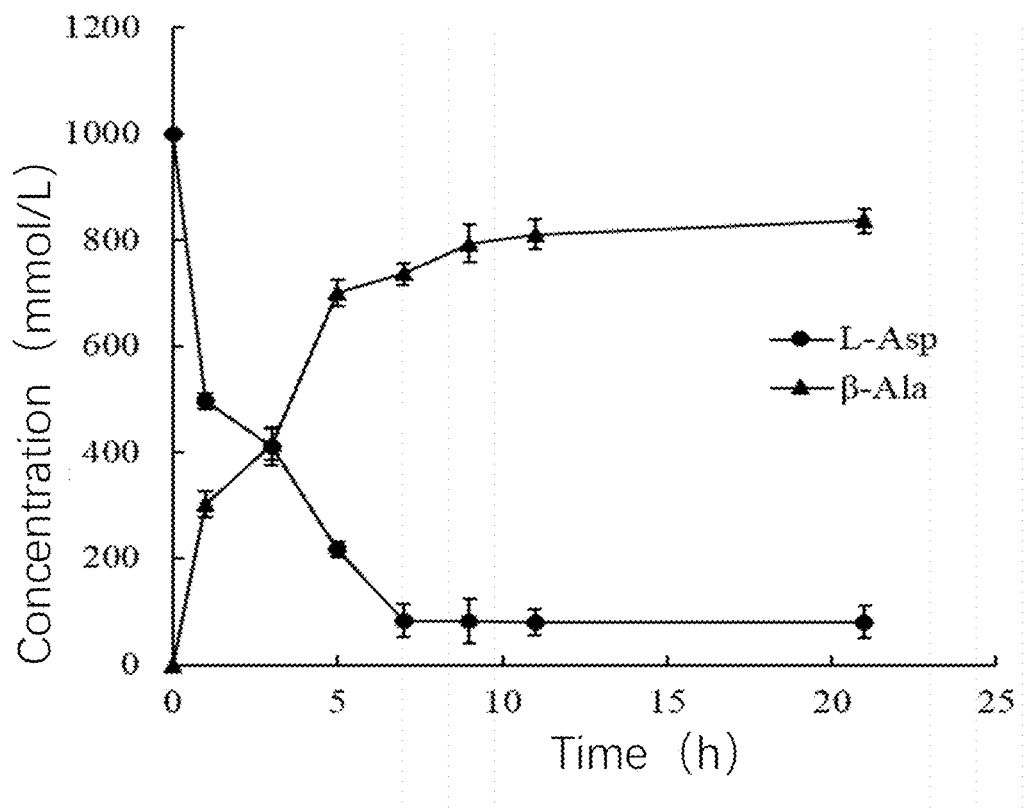
FIG. 3 shows the catalysis effect of a wild-type strain with high concentration of substrate added once.

Example 2 Catalysis Process of Wild-Type Strain with High-Concentration Solid Substrate Added Once The cells of the wild-type strain were cultured according to the method of step (3) of Example 1, and the cells induced by IPTG were collected by centrifugation for whole-cell catalysis reaction. In a 10 mL reaction system (including bacterial cells, a phosphate buffer with pH of 6.5, the substrate, and PLP), wherein the OD$_{600}$ of the cells was 200, the pH was 6.5, the PLP concentration was 1 mmol/L, and the reaction temperature was 35-37° C., the solid substrate sodium L-aspartate was added once to a final concentration of 1 mol/L. Samples were taken at regular intervals to detect the yield of β-alanine. The results are shown in FIG. 3. The concentration of β-alanine converted after 10 h of reaction was 836 mmol/L, and the molar conversion rate was 83.6%.

Example 3 Whole-Cell Catalysis Process of Batch Feeding of Substrate

Figure 4A:
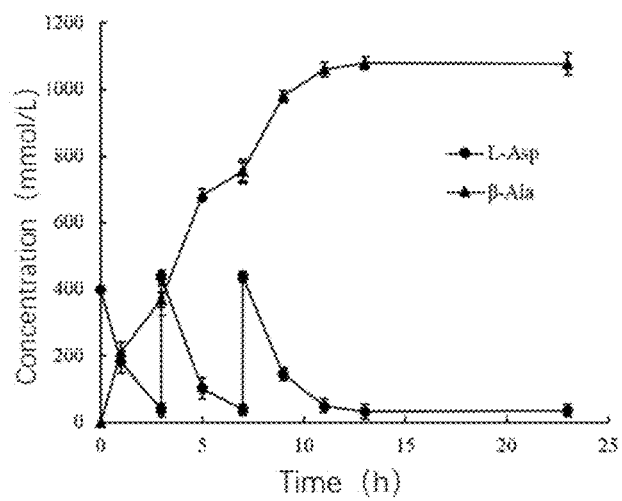
FIG. 4A shows the wild-type strain whole cell catalysis effect after substrates added 3 times.
Figure 4B:
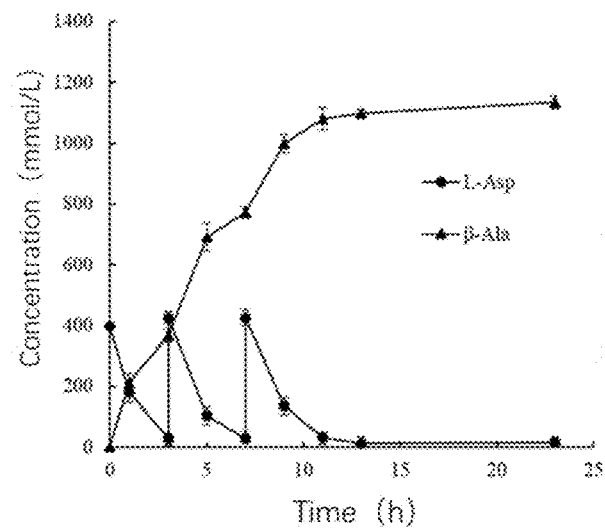
FIG. 4B shows the K221R strain whole cell catalysis effect after substrates added 3 times.
Figure 4C:
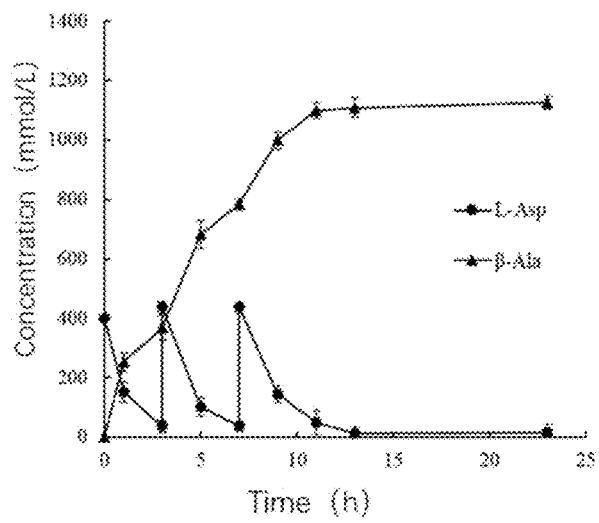
FIG. 4C shows the G369A strain whole cell catalysis effect after substrates added 3 times.

The wild-type strain and the cells expressing the recombinant E. coli BL21/pET28a-K221R and BL21/pET28a-G369A were used as cell catalysts, 0.4 mol/L solid substrate was added to the reaction system with a volume of 10 mL and an OD$_{600}$ of 200 every 4 h. The solid substrate was added three times and the yield of products was detected. The concentration of β-alanine transformed by the wild-type strain was 1079.98 mmol/L, about 96.22 g/L, and the molar conversion rate was 89.90% (FIG. 4A), with a small amount of substrate remained. After the substrate was added three times, the β-alanine transformed by the K221R mutant strain was 1135.4 mmol/L, about 101.15 g/L, and the molar conversion rate was 94.62% (FIG. 4B), with no substrate remained. After the substrate was added three times, the β-alanine transformed by the G369A mutant strain was 1127.43 mmol/L, about 100.44 g/L, and the molar conversion rate was 93.95% (FIG. 4C), with no substrate remained.

Figure 5A:
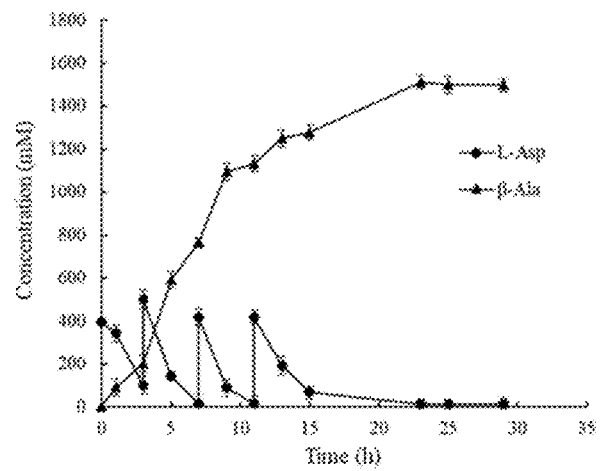
FIG. 5A shows the K221R strain whole cell catalysis effect after substrates added 4 times.
Figure 5B:
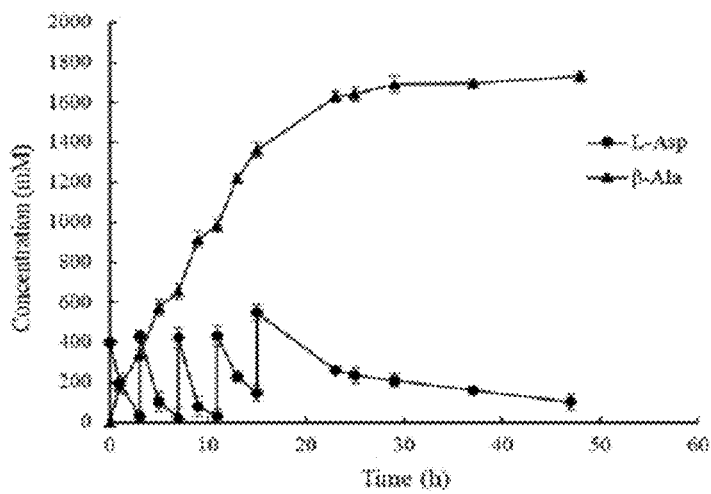
FIG. 5B shows the K221R strain whole cell catalysis effect after substrates added 5 times.
Figure 5C:
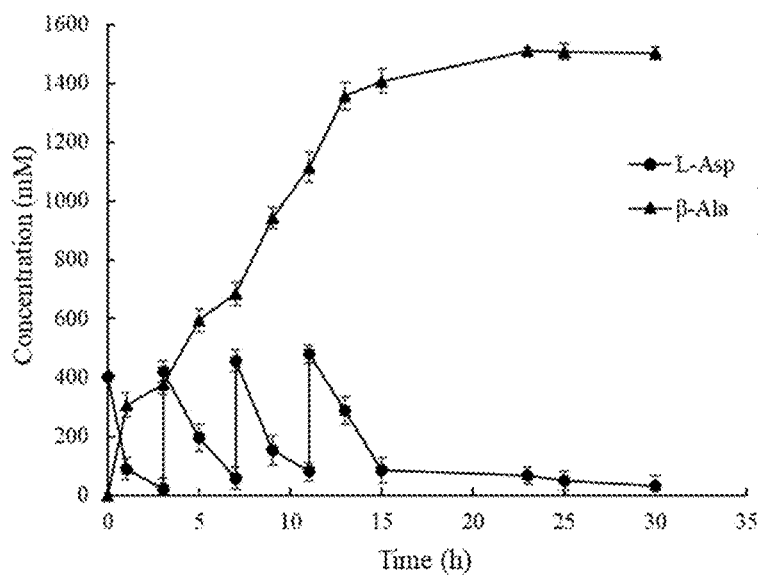
FIG. 5C shows the G369A strain whole cell catalysis effect after substrates added 4 times.
Figure 5D:
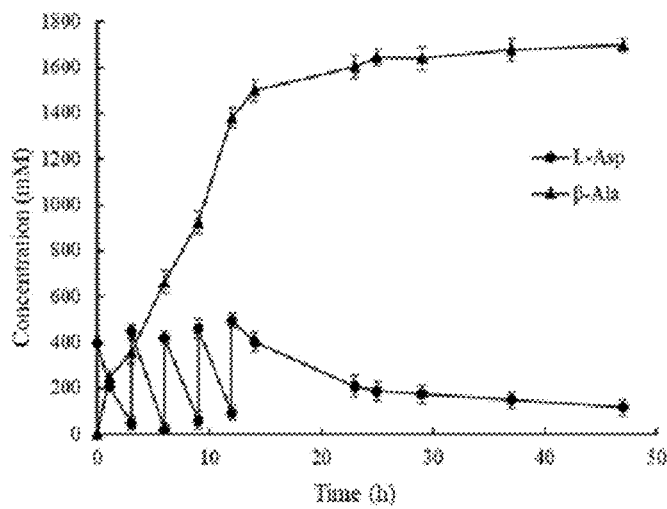
FIG. 5D shows the G369A strain whole cell catalysis effect after substrates added 4 times.

Example 4 Optimization of Number of Times of Batch Feeding Addition of Substrate The substrate was added to the whole cell catalytic system for different number of times, and the effects of batch feeding of different number of times on the catalytic effect were compared. When the substrate was added four times during the catalytic reaction, the mutant strain K221R could produce 1512.24 mmol/L β-alanine, about 134.72 g/L, and the molar conversion rate was 94.52% (FIG. 5A), with no substrate remained. When the substrate was added five times during the catalytic reaction, the mutant strain K221R could produce 1729.71 mmol/L β-alanine by transformation, about 154.05 g/L, and the molar conversion rate was 86.49% (FIG. 5B), with a small amount of substrate remained. When the substrate was added four times during the catalytic reaction, the mutant strain G369A could produce 1530.27 mmol/L β-alanine by catalysis, about 136.33 g/L, and the molar conversion rate was 95.64% (FIG. 5C), with no substrate remained. When the substrate was added five times during the catalytic reaction, the mutant strain G369A could produce 1698.42 mmol/L β-alanine by transformation, about 151.31 g/L, and the molar conversion rate was 84.92% (FIG. 5D), with a small amount of substrate remained.

Example 5 High-Density Fermentation of Recombinant E. coli and Whole Cell Catalytic Production of β-Alanine Recombinant E. coli BL21/pET28a-K221R and BL21/pET28a-G369A were respectively inoculated into 5 mL of LB culture medium containing kanamycin at a concentration of 50 μg/mL, and cultured overnight at 37° C. and 200 rpm with shaking. The overnight culture was inoculated into an 2YT culture medium containing kanamycin at a concentration of 50 μg/mL at an inoculum concentration of 1%, and cultured with shaking at 37° C. and 200 rpm for 6-8 h. The culture was respectively inoculated into a 2 L fermenter fermentation culture medium containing kanamycin at a concentration of 50 μg/mL at an inoculum concentration of 6-8%, and cultured at 37° C. When the $OD_{600}$ reaches 60-70, the temperature was reduced to 28-30° C., IPTG was added to a final concentration of 0.8 mmol/L, and the fermentation was ended after induction culture for 36-40 h.

Figure 6A:
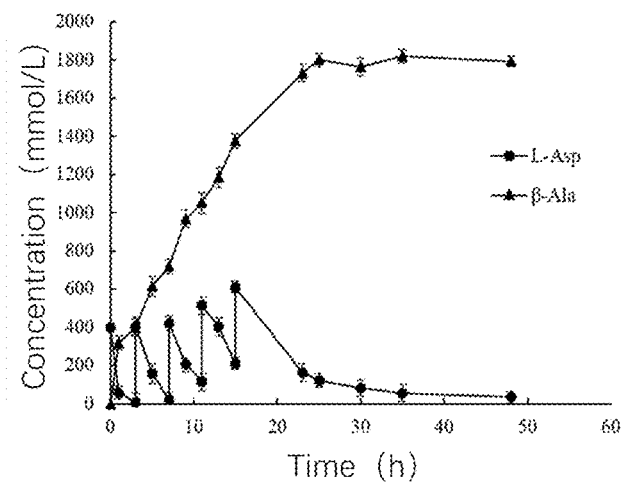
FIG. 6A shows the effect of high-density fermentation strain K221R for whole-cell catalytic production of β-alanine.
Figure 6B:
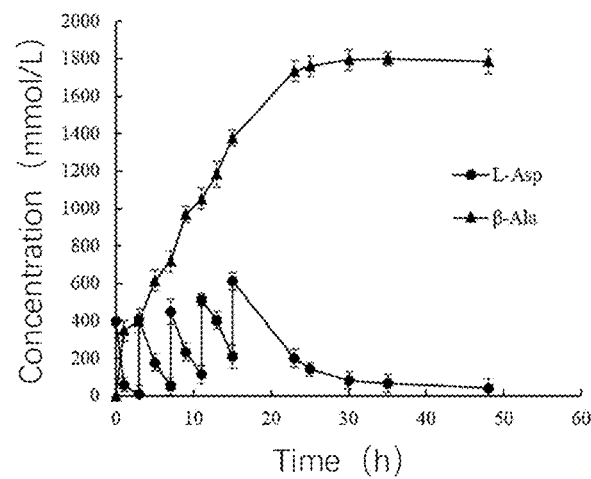
FIG. 6B shows the effect of high-density fermentation strain G368A for whole-cell catalytic production of β-alanine.

The bacteria solution after high-density fermentation was centrifuged, and cells were collected, washed with water, and centrifuged and collected again. In a 50 mL reaction system, wherein the $OD_{600}$ of the cells was 200, the pH was 6.5, the PLP concentration was 1 mmol/L, and the reaction temperature was 35-37° C., 0.4 mol/L solid substrate was added in batches and continuously stirred. When the substrate reacted completely, a next batch of substrate was added, and the content of each component in the reaction solution was detected by HPLC. The results are shown in FIG. 6A and FIG. 6B. The strain expressing K221R produced 1820.04 mmol/L β-alanine by transformation, about 162.15 g/L, and the molar conversion rate was 91.00% (FIG. 6A), with no remaining substrate. The strain expressing G369A produced 1800.70 mmol/L β-alanine by transformation, about 160.42 g/L, and the molar conversion rate was 90.04% (FIG. 6B), with no substrate remained.

Although the disclosure has been disclosed as above in preferred examples, it is not intended to limit the disclosure. Anyone familiar with this technology can make various changes and modifications without departing from the spirit and scope of the disclosure. Therefore, the protection scope of the disclosure should be defined by the claims.

---

What is claimed is:

1. An L-aspartate α-decarboxylase mutant, comprising the amino acid sequence set forth in SEQ ID NO:1 or SEQ ID NO:2.

2. A method for producing β-alanine, which comprises:
incubating the L-aspartate α-decarboxylase mutant of claim 1 in the presence of sodium L-aspartate under conditions that yield transformation of the L-aspartate to β-alanine.

3. A method of whole cell transformation of L-aspartate to produce β-alanine, which comprises:
culturing *Escherichia coli* (*E. coli*) BL21 cells comprising an expression vector encoding the L-aspartate α-decarboxylase mutant of claim 1 in a medium under conditions that cause expression of the L-aspartate α-decarboxylase mutant to produce a bacterial solution comprising whole *E. coli* BL21 cells expressing the L-aspartate α-decarboxylase mutant, and
adding sodium L-aspartate to the bacterial solution to produce β-alanine by whole cell transformation.

4. A cell comprising a gene encoding an L-aspartate α-decarboxylase mutant that comprises the amino acid sequence set forth in SEQ ID NO: 1 or SEQ ID NO: 2.

5. The cell of claim 4, wherein the cell is an *Escherichia coli* (*E. coli*) BL21 cell.

6. The cell of claim 5, further comprising a pET28a expression vector, and wherein the pET28a expression vector encodes the amino acid sequence set forth in SEQ ID NO: 1 or SEQ ID NO: 2.

7. A method for constructing a cell having a gene encoding an L-aspartate α-decarboxylase mutant, which comprises:
ligating a gene encoding an L-aspartate α-decarboxylase mutant with an expression vector to obtain an expression vector encoding the L-aspartate α-decarboxylase mutant, wherein the L-aspartate α-decarboxylase mutant comprises the amino acid sequence set forth in SEQ ID NO: 1 or SEQ ID NO: 2, and
transforming the expression vector encoding the L-aspartate α-decarboxylase mutant into *Escherichia coli* (*E. coli*).

* * * * *